(12) United States Patent
Kawano et al.

(10) Patent No.: US 7,500,951 B2
(45) Date of Patent: Mar. 10, 2009

(54) LESION DETECTING SYSTEM

(75) Inventors: Hironao Kawano, Hachioji (JP); Hironobu Takizawa, Hachioji (JP); Akio Uchiyama, Yokohama (JP); Masatoshi Homan, Hino (JP); Hidetake Segawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 723 days.

(21) Appl. No.: 11/036,239

(22) Filed: Jan. 14, 2005

(65) Prior Publication Data

US 2005/0159642 A1 Jul. 21, 2005

(30) Foreign Application Priority Data

Jan. 16, 2004 (JP) ............................. 2004-009766

(51) Int. Cl.
*A61B 5/00* (2006.01)

(52) U.S. Cl. .................. 600/309; 600/310; 600/343; 600/317

(58) Field of Classification Search ................ 600/309, 600/347, 348, 350, 353, 424, 427, 476; 128/899; 422/57, 58; 604/891.1
See application file for complete search history.

(56) References Cited

U.S. PATENT DOCUMENTS

| 5,167,626 A | 12/1992 | Casper et al. | |
|---|---|---|---|
| 6,126,903 A * | 10/2000 | Preston et al. | ................ 422/99 |
| 2001/0051766 A1* | 12/2001 | Gazdzinski | ................ 600/309 |
| 2002/0060565 A1* | 5/2002 | Tondra | ................ 324/260 |
| 2002/0111544 A1 | 8/2002 | Iddan | |
| 2002/0132226 A1 | 9/2002 | Nair et al. | |
| 2002/0146368 A1* | 10/2002 | Meron et al. | ................ 424/1.49 |
| 2003/0153067 A1* | 8/2003 | Stett et al. | ................ 435/285.2 |
| 2004/0011671 A1* | 1/2004 | Shults et al. | ................ 205/777.5 |

FOREIGN PATENT DOCUMENTS

| EP | 0 554 955 A1 | 8/1993 |
|---|---|---|
| JP | 5-200015 | 8/1993 |
| JP | 6-23020 | 2/1994 |
| JP | 2004-516863 | 6/2004 |
| WO | WO 92/05822 | 4/1992 |
| WO | WO 97/33513 | 9/1997 |
| WO | WO 99/48419 | 9/1999 |
| WO | WO 01/53792 A2 | 7/2001 |
| WO | WO 01/69212 A1 | 9/2001 |
| WO | WO 02/00758 A1 | 1/2002 |
| WO | WO 2004/014227 A1 | 2/2004 |

* cited by examiner

*Primary Examiner*—Long V Le
*Assistant Examiner*—Saurel J Selkin
(74) *Attorney, Agent, or Firm*—Scully, Scott, Murphy & Presser, P.C.

(57) ABSTRACT

A capsule medical apparatus includes a reaction plane on which one or more kinds of reacting substance reacting with an internal substance in the body to be examined are fixed, wherein the reacting substance is chemical reacting substance or biochemical reacting substance, and an analyzer detects and analyzes the substance reacted with the reaction plane or a trace of the reaction outside of the body to be examined.

34 Claims, 7 Drawing Sheets

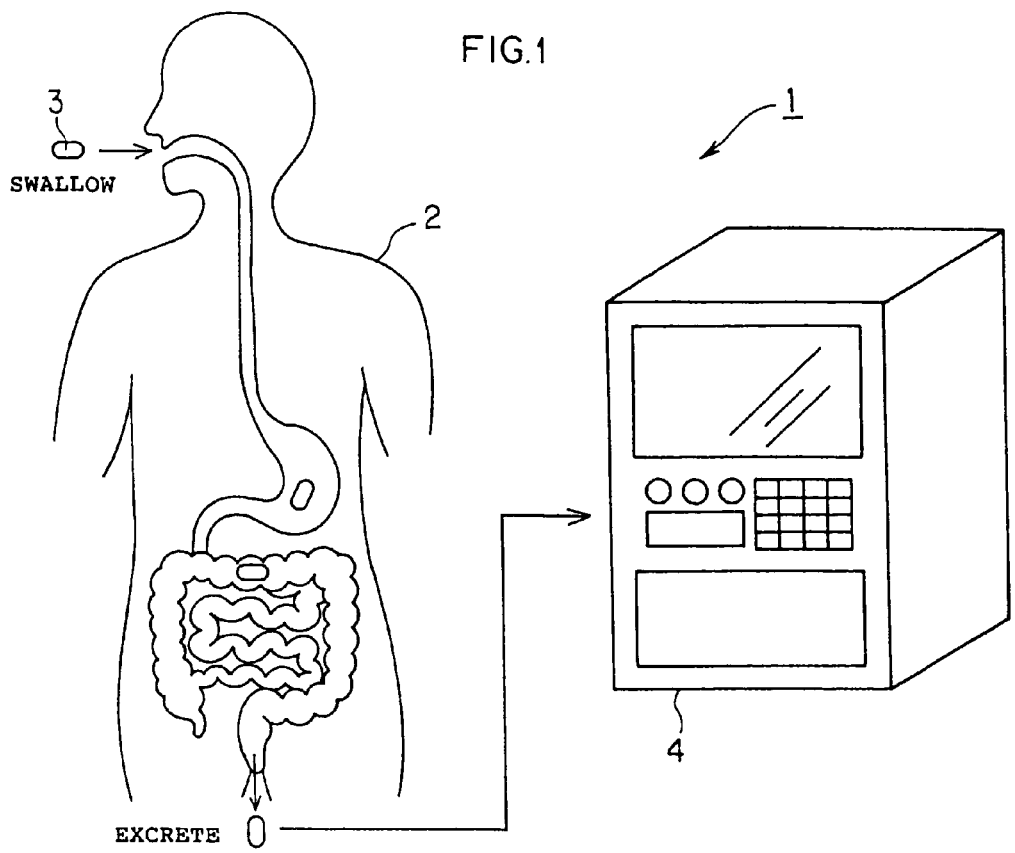
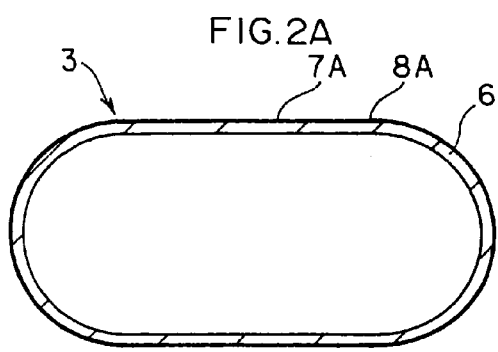
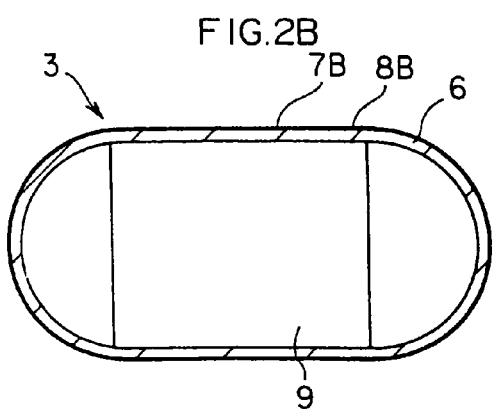

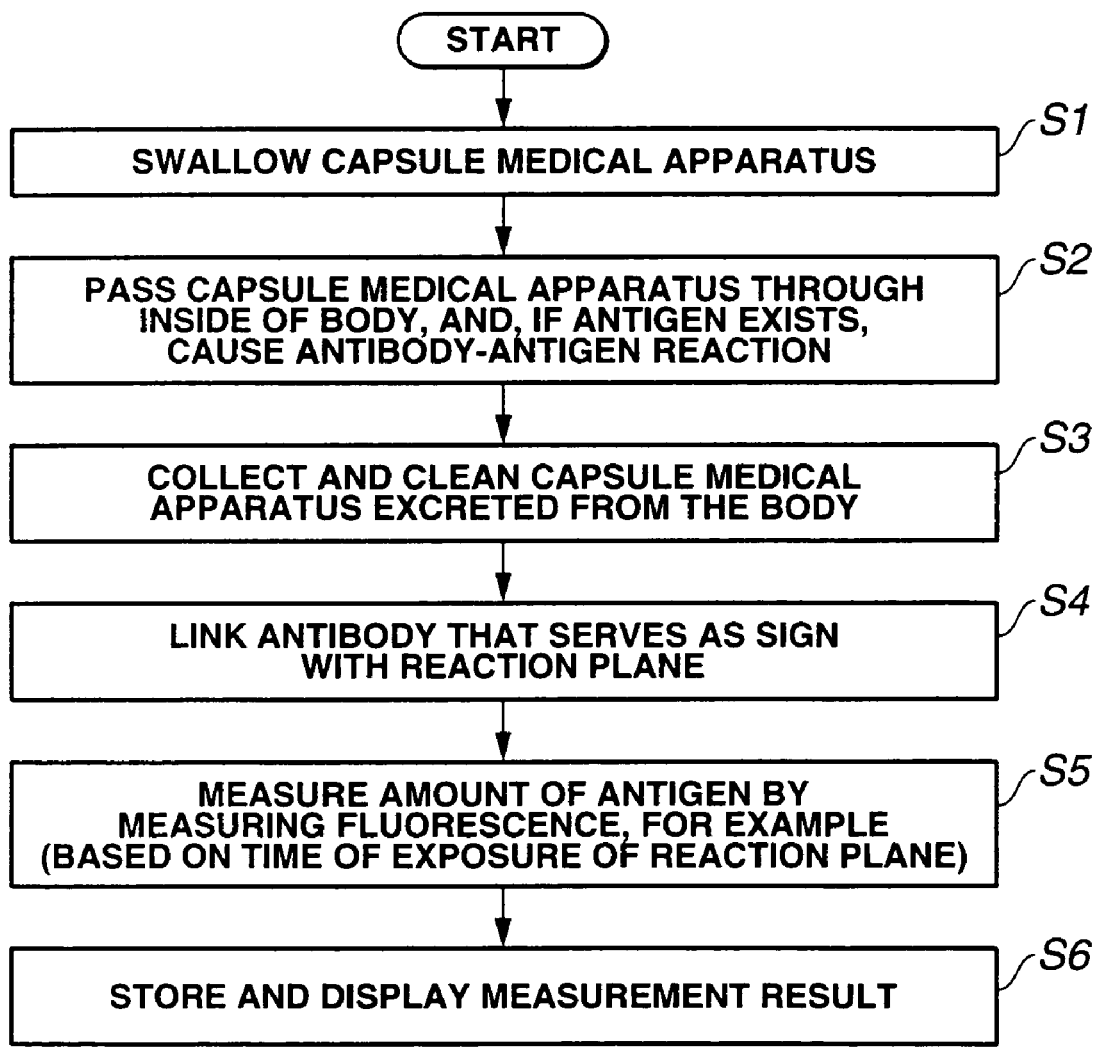

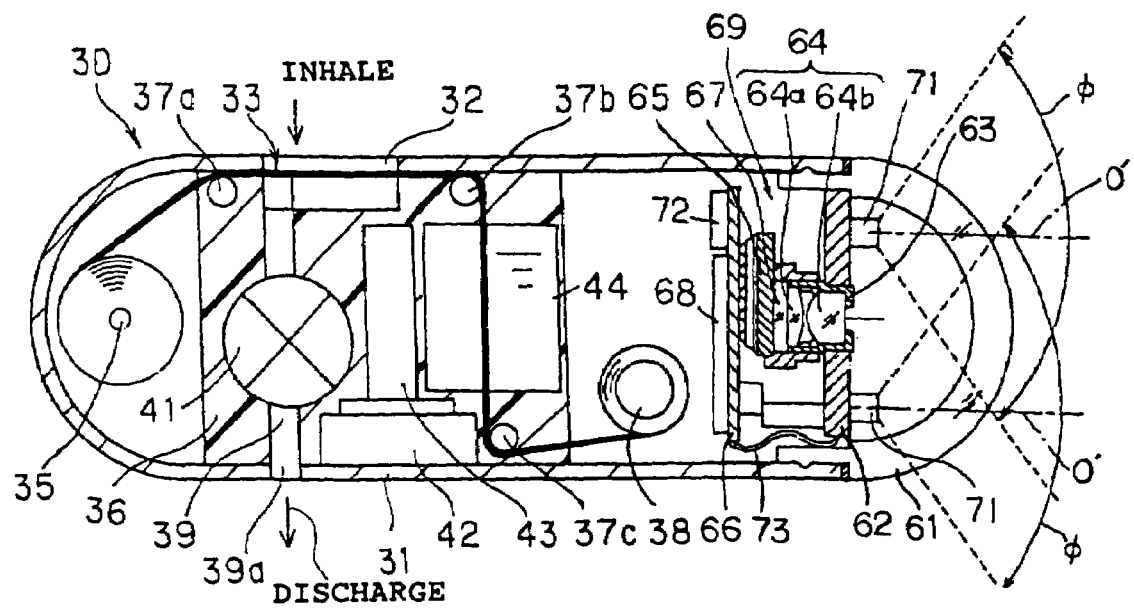
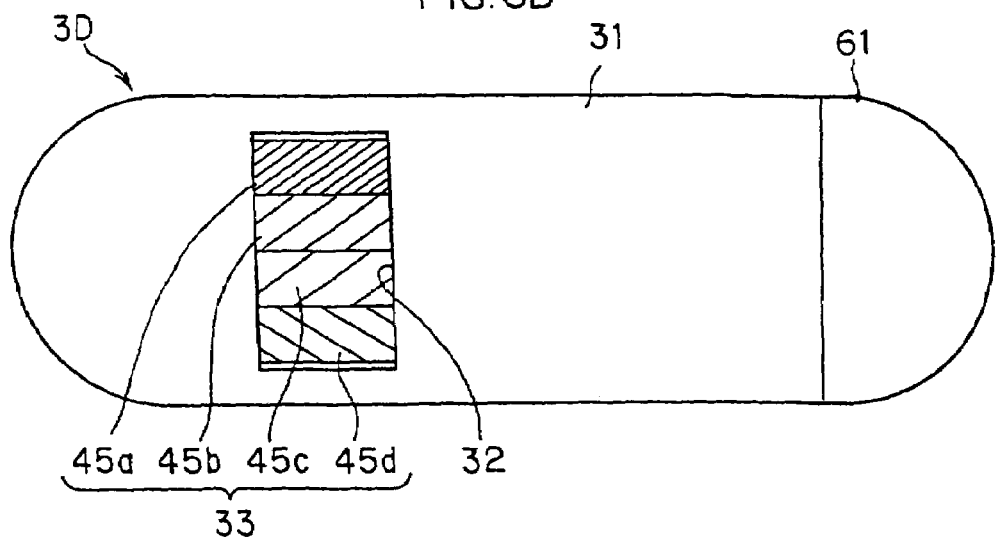

LESION DETECTING SYSTEM

This application claims benefit of Japanese Application No. 2004-009766 filed on Jan. 16, 2004, the contents of which are incorporated by this reference.

BACKGROUND OF THE INVENTION

1. Field of the Invention

The present invention relates to a lesion detecting system to be brought into a body to be examined for detecting a lesion by using the reaction with a tumor marker, bleeding and so on.

2. Description of the Related Art

Current digestive cancer screening is performed by examining occult blood in feces and examining blood. Examination of occult blood in feces is a technology for detecting the presence of bleeding in a digestive tract from feces of a subject. Blood examination is a technology for diagnosing the presence of a cancer by detecting an amount of a tumor marker contained in serum.

In addition, detection of a tumor marker ejected from a digestive cancer in feces has been attempted.

Furthermore, Japanese Unexamined Patent Application Publication No. 5-200015 discloses a medical capsule apparatus for sucking bodily fluids in a body cavity of a living body and examining the sucked bodily fluid.

SUMMARY OF THE INVENTION

A lesion detecting system of the invention includes a capsule medical apparatus including a reaction plane on which one or more kinds of chemical reacting substance or biochemical reacting substance reacting with an internal substance in the body to be examined are fixed, and an analyzer for detecting and analyzing the substance reacted with the reaction plane or a trace of the reaction outside of the body to be examined.

BRIEF DESCRIPTION OF THE DRAWINGS

FIG. 1 is a diagram showing a lesion detecting system according to a first embodiment of the invention;

FIG. 2A is a longitudinal section view showing a construction example of a capsule medical apparatus;

FIG. 2B is a longitudinal section view showing another construction example of the capsule medical apparatus;

FIG. 4 is a flowchart describing a typical example of operational details;

FIG. 6A is a longitudinal section view showing a construction of a capsule medical apparatus according to a second embodiment of the invention;

FIG. 6B is a plan view of FIG. 6A;

DESCRIPTION OF THE PREFERRED EMBODIMENTS

Figure 2C:
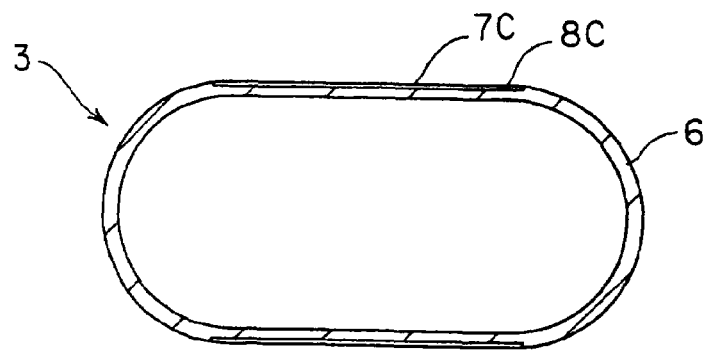
FIG. 2C is a longitudinal section view showing another construction example of the capsule medical apparatus.

Embodiments of the invention will be described below with reference to drawings.

First Embodiment

A first embodiment of the present invention will be described with reference to FIGS. 1 to 5.

As shown in FIG. 1, a lesion detecting system 1 according to a first embodiment of the present invention includes a capsule medical apparatus 3 and an analyzer 4. The capsule medical apparatus 3 is swallowed by a patient 2 serving as a subject from his/her mouth and includes a reaction plane to be reacted with an antigen acting as an internal substance such as a tumor part and a bleeding part in the body of the patient 2. The analyzer 4 detects and analyzes an antigen reacting with the reaction plane of the capsule medical apparatus 3 excreted to the outside of the patient 2 and collected therefrom.

As shown in FIG. 2A, the capsule medical apparatus 3 may include a film 8A having a reaction plane 7A on the outer surface of a container 6 serving as a hollow casing in a capsule form. In this case, an antibody specifically reacting with a tumor marker, a blood component and so on is fixed on the reaction plane 7A. Alternatively, the capsule medical apparatus 3 may include a film 8B having a reaction plane 7B on which a magnetic antibody is fixed. In this case, a permanent magnet 9 may be provided within the container 6. Providing the permanent magnet 9 can prevent the scattering and losing the antibody.

Alternatively, as shown in FIG. 2C, a film 8C having a reaction plane 7C may be attached to a cylindrical part on the outer circumference of the container 6 with, for example, an adhesive. In this case, after the capsule medical apparatus 3 is collected outside of the body, the film 8C on the cylindrical surface part can be removed easily.

The capsule medical apparatus 3 shown in FIGS. 2A to 2C have the reaction planes 7A to 7C, which are always exposed so that the costs can be reduced. Furthermore, since a transmitter is not required, the size of the capsule medical apparatus 3 can be reduced easily.

Protein that reacts with an internal substance may be fixed onto the reaction plane 7A. More specifically, protein that bonds with an internal substance such as lecithin may be fixed, and an analysis may be made on whether a tumor marker specifically occurring in a lesion part and/or an internal substance such as a blood component are contained in the internal substance bonding with the reaction plane after the excretion.

Figure 3A:
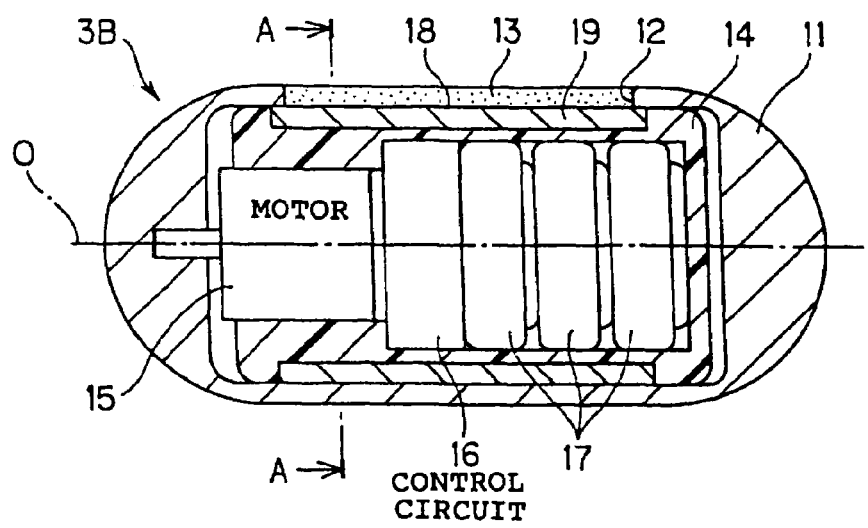
FIG. 3A is a longitudinal section view showing a construction of a capsule medical apparatus having a structure controlling the exposure of a reaction plane.
Figure 3B:
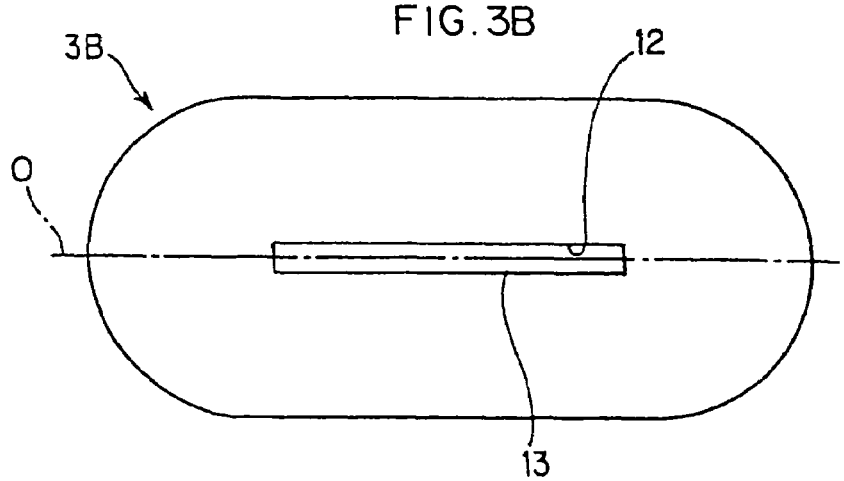
FIG. 3B is a plan view of the capsule medical apparatus in FIG. 3A.
Figure 3C:
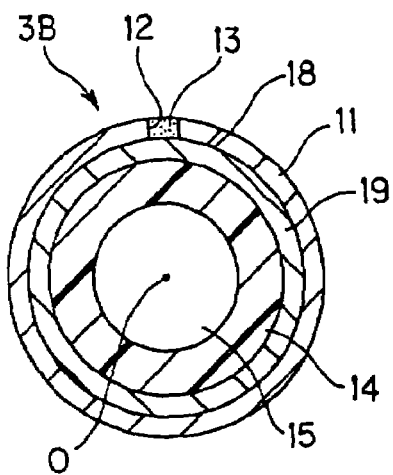
FIG. 3C is a section view taken at the line A-A in FIG. 3A.

On the other hand, the capsule medical apparatus 3B shown in FIGS. 3A to 3C has a structure for controlling the reaction plane to be exposed in time so that an internal position or time of a reaction with an antigen can be detected or analyzed with high precision.

FIG. 3A shows a longitudinal section of the capsule medical apparatus 3B. FIG. 3B shows a plan view of FIG. 3A. FIG.

Figure 3D:
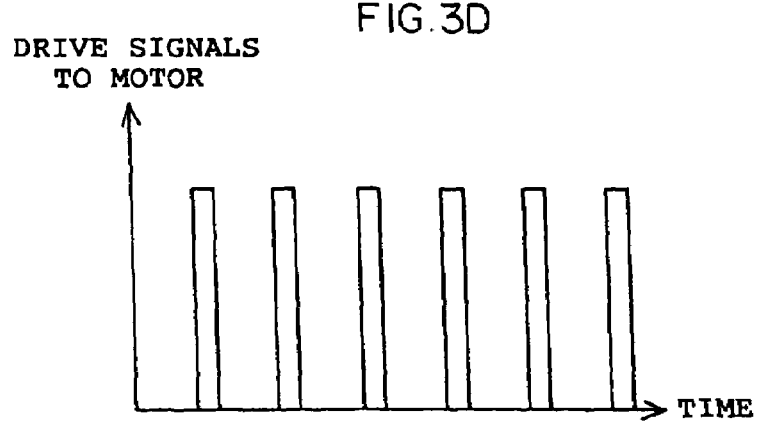
FIG. 3D is a diagram showing drive signals that drive a motor contained in the capsule medical apparatus.

3C shows a section taken at the line A-A in FIG. 3A. FIG. 3D shows a drive signal example that drives a motor contained therein.

As shown in FIGS. 3A to 3C, the capsule medical apparatus 3B includes a through-hole 12 in a slit form at, for example, one part on the outer circumference of an exterior 11 in a capsule form and has a cylindrical storage section within the exterior 11. The storage section communicates with the outside through the through-hole 12. A filter 13 that is a porous member for filtering bodily fluids is placed in the through-hole 12, and a cabinet 14 is placed in the internal part. A film 19 having a reaction plane 18 is attached onto the outer circumference of the cabinet 14.

In other words, the cylindrical cabinet 14 is fitted to and rotatably stored in the cylindrical storage section under the through hole 12 having the filter 13 therein. The body of a motor 15 is fixed in the inner part of one end of the cabinet 14. The axis of rotation projecting from the motor 15 on the center axis of the cabinet 14 is fixed by, for example, press-fitting to a concave on the center axis of the exterior 11.

A control circuit 16 and a battery 17 are attached within the cabinet 14. The control circuit 16 is adjacent to the motor 15 and rotationally drives the motor 15. The battery 17 supplies power to the control circuit 16 and the motor 15. The film 19 is provided on the outer circumference of the cabinet 14. The film 19 has a width, which is slightly larger than the longitudinal size of the through-hole 12, and has the reaction plane 18 on which an antibody is fixed.

Driving the motor 15 rotationally drives, with respect to the exterior 11, the cabinet 14 side fitted into and stored within the exterior 11. Since the film 19 having the reaction plane 18 is attached to the outer circumference of the cabinet 14, the reaction plane 18 moves over time with respect to the through-hole 12 in the exterior 11. Thus, the reaction plane 18 can be used for antigen detection in time series.

In this case, the motor 15 intermittently rotates in response to, for example, pulse-shaped drive signals as shown in FIG. 3D under the control of the control circuit 16. More specifically, as shown in FIG. 1, the reaction plane 18 is defined to make one turn with respect to the through hole 12 in the cylindrical film 19 in 5 to 8 hours, which are required on average from the swallowing of the capsule medical apparatus 3B by the patient 2 to the excretion thereof from the body of the patient 2. Notably, the film 19 include a marker, not shown, indicating an initial position of a reaction and the divisions at regular intervals of a scale.

Furthermore, the capsule medical apparatus 3 or 3B is collected after excreted from the body, and an antigen reacting on the reaction plane 7A or 18 is detected and analyzed by the analyzer 4.

In the case of the capsule medical apparatus 3 in FIG. 2C or a capsule medical apparatus 3B in FIG. 3, the film 8C or 19 is removed from the capsule medical apparatus 3 or capsule medical apparatus 3B to detect and analyze an antigen by a method illustrated in FIG. 4, for example.

Next, operations of this embodiment will be described.

In order to examine the inside of the body by, for example, cancer screening, the patient 2 swallows the capsule medical apparatus 3 or 3B as shown in FIG. 1 in step S1. The swallowing sends the capsule medical apparatus 3 or 3B to the inside of the body. As shown in FIG. 1, the swallowed capsule medical apparatus 3 or 3B passes through the esophagus, stomach, small intestine and then colon and is excreted from the anus to the outside. In this way, the capsule medical apparatus 3 or 3B sequentially passes through the esophagus, stomach, small intestine and colon until excreted to the outside.

In step S2, when an antigen to be examined exists in the body while the capsule medical apparatus 3 or 3B is sequentially passing through the esophagus, stomach and so on, the reaction planes 7A to 7C or reaction plane 18 exposing to the outside specifically reacts with the antigen, that is, the antigen-antibody reaction is caused.

Then, in step S3, the patient 2 or a medical staff collects and cleans the capsule medical apparatus 3 or 3B excreted from the body.

Next, in step S4, a medical staff uses the analyzer 4 to bond an antibody serving as a label (labeled antibody or labeled molecule) to the antibody having undergone the antigen-antibody reaction on the reaction planes 7A to 7C or reaction plane 18 of the cleaned capsule medical apparatus 3 or 3B.

The antibody serving as a label may be a fluorescent substance (fluorescent immunoassay in this case) or a light-emitting substance (light-emitting immunoassay in this case).

After the antibody serving as a label, that is not bonded, is removed by cleaning, for example, an amount of fluorescence or light emission of the bonded antibody serving as the label is measured in next step S5 to measure an amount of the antigen.

In the case of the capsule medical apparatus 3B, based on the marker indicating the initial position of the reaction and the divisions at regular intervals on the film 19, a time that the reaction plane 18 is exposed at the position of the through-hole 12 is measured. Then, the amount of the detected antigen is measured based on the time. Then, in step S6, the measurement result is associated with the time and is stored and/or displayed. Then, the processing ends.

Furthermore, when an antigen is detected, a time that the reaction plane 18 was exposed can be calculated based on the position where the antigen was detected. The time can be used to estimate the approximate part in the body where the antigen was detected, and close examinations and so on thereafter can be performed more smoothly.

According to this embodiment, when the capsule medical apparatus 3 shown in FIGS. 2A to 2C is used, a tumor or internal substance such as bleeding to be examined can be detected at low costs.

Also in both of the capsule medical apparatus 3 and 3B, an antigen-antibody reaction is caused on the reaction plane before the antigen characteristic of a tumor marker or blood component is lost in the vicinity of a tumor part or bleeding part. Thus, the tumor marker or blood component can be detected more accurately.

Instead of the detection of an occurring antigen-antibody reaction within the capsule medical apparatus, the capsule medical apparatus may be removed from the patient 2 serving as a subject may set to the analyzer 4 that performs detection and/or analysis (that is, a measuring part therefor may be provided outside of the body to be examined). Thus, the size of the capsule medical apparatus to be introduced into the inside of the body to be examined can be reduced.

In other words, since, in both of the capsule medical apparatus 3 and 3B, a detector or analyzer is not required therein and a unit for transmission to the outside of the body is not required, the size of the capsule medical apparatus 3 and 3B can be reduced. Furthermore, the costs can be reduced.

When the capsule medical apparatus 3B shown in FIG. 3A, for example, is used, the reaction plane 18 to be exposed is controlled in time. Thus, the approximate position of a reacting antigen can be detected. Furthermore, the active state of an antibody on the reaction plane 18 can be maintained until the reaction.

Since the reaction plane 18 is controlled to cover not to be exposed after the reaction plane 18 is exposed for a predetermined period of time, changes in state of the reacting of the reaction plane 18 can be prevented, which allows detection of an amount of an antigen with high precision. Furthermore, a detection result can be obtained from detection of an amount of antigen at every part that the capsule medical apparatus 3B passes through in the body.

Furthermore, the use of a marker indicating the initial position of reaction facilitates the visual check of the starting part of the reaction on the film 19.

Furthermore, since the filter 13 is provided in the through-hole 12 to be reacted, unnecessary articles such as solid substances in bodily fluids do not enter into the through-hole 12. Thus, the clogging thereof can be prevented. Furthermore, chemical stability within the capsule medical apparatus 3B during and after a reaction can be maintained.

Figure 3E:
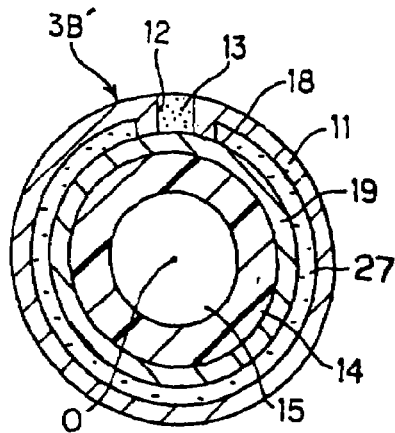
FIG. 3E is a section view of a capsule medical apparatus according to a variation example thereof.

Furthermore, in the capsule medical apparatus 3B shown in FIGS. 3A to 3C, the part not exposed, through the through-hole 12, in the reaction plane 18 of the film 19 may be soaked in a preservative fluid. The construction of the variation example is shown in FIG. 3E. The lateral section view corresponds to the section taken at the line A-A in FIG. 3A.

A capsule medical apparatus 3B' shown in FIG. 3E differs from, for example, the capsule medical apparatus 3B shown in FIG. 3C in that an enclosed space outside of the reaction plane 18 on the outer circumference of the film 19 is filled with a preservative fluid 27.

In other words, the capsule medical apparatus 3B' differs from the capsule medical apparatus 3B shown in FIG. 3C in that a notch or the like is provided at a part facing toward the reaction plane 18 of the film 19 on the inner circumference of the exterior 11 excluding the part around the through-hole 12 to provide a space having a lateral section in a ring shape and a preserving unit is provided in the space. The preserving unit is filled with the preservative fluid 27.

Then, the structure for exposure control is maintained in which the cabinet 14 with the film 19 attached is rotated to expose the part of the reaction plane 18 through the through hole 12 and to soak the other part of the reaction plane 18 not exposed through the through-hole 12 in the preservative fluid 27 at all times.

Thus, according to this variation example, in addition to the operations and advantages of the capsule medical apparatus 3B, an antibody before a reaction can be maintained at a stable state, and an antigen and antibody after a reaction can be maintained at a stable state.

Figure 5:
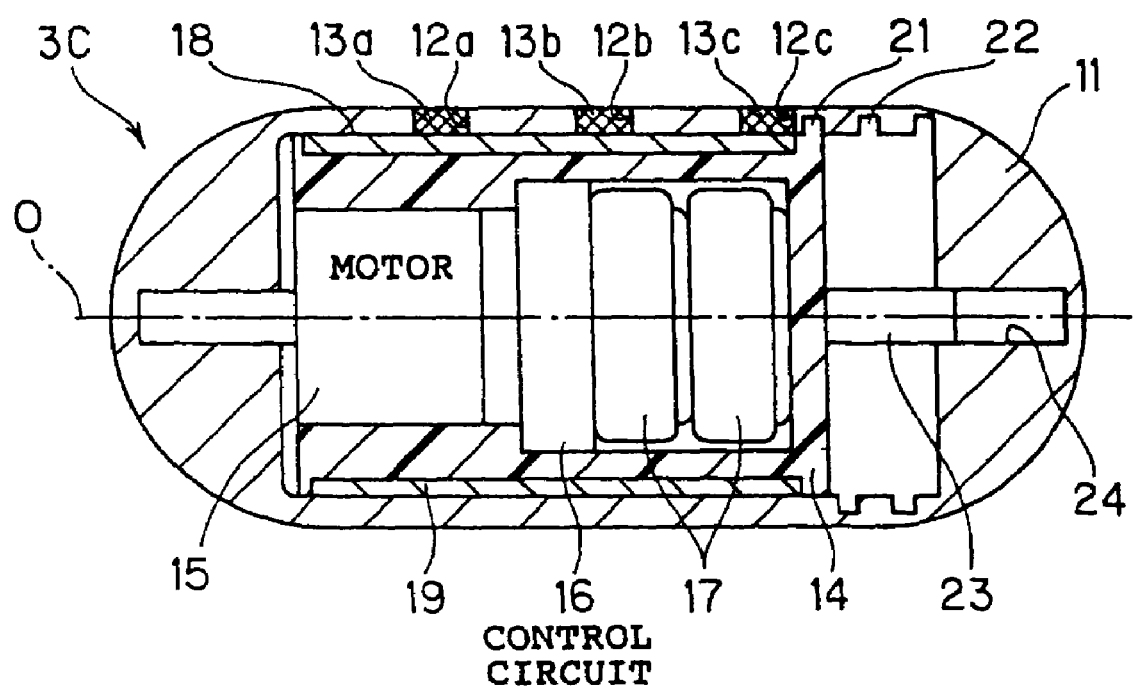
FIG. 5 is a longitudinal section view showing a construction of a capsule medical apparatus according to the variation example.

Like the capsule medical apparatus 3C of the variation example shown in FIG. 5, the cabinet 14 side may be helically rotated and moved with respect to the exterior 11.

In the case in FIG. 5, a pin 21 projects from the cabinet 14, and the pin 21 is engaged in a spiral groove 22 on the inner circumference of the exterior 11. Furthermore, a guide axis 23 projects from the opposite side of the axis of rotation of the motor 15 on the center axis O of the cabinet 14 and is engaged in a guide hole 24 in the exterior 11. Moreover, the axial length of the cabinet 14 side is defined shorter than the axial length of the storage section provided by the exterior 11, and, in the case in FIG. 5, the cabinet 14 side can be moved to the right by a predetermined distance.

When the motor 15 is rotationally driven, the cabinet 14 side is rotated. Here, the pin 21 projecting from the cabinet 14 helically moves along the spiral groove 22. In the case in FIG. 5, the cabinet 14 side helically rotates and moves to the right within the exterior 11.

Furthermore, in the case in FIG. 5, the exterior 11 has three through-holes 12a, 12b and 12c, for example, and filters 13a, 13b and 13c are attached to the through-holes 12a, 12b and 12c, respectively.

The filters 13a, 13b and 13c are formed of meshes of platinum fiber. The platinum fiber has an average diameter of about 0.5 to 0.8 micron, and blood and/or living-body tissue are not easily adhered to and coagulated in the platinum fiber. Therefore, the filtering function can be maintained for many hours, and antigens can be detected with high precision for many hours.

In this variation example, different kinds of antibody can be fixed to the reaction plane 18 of the film 19 sequentially exposed through the through-holes 12a, 12b and 12c. In this case, multiple kinds of tumor marker and so on, which will be described in a second embodiment below, can be adopted. The other construction is basically the same construction as the one in FIG. 3, and the same reference numerals are given to the same components, the description of which will be omitted.

According to this variation example, the exposure of the reaction plane 18 can be controlled in longer hours.

Second Embodiment

Next, a second embodiment of the invention will be described with reference to FIGS. 6A and 6B. FIG. 6A shows a section view of an internal structure of a capsule medical apparatus 3D according to the second embodiment, and FIG. 6B shows a plan view of FIG. 6A. The capsule medical apparatus 3D has an opening part 32 in an exterior 31 having a capsule form so that the exposure/unexposure of a film 34 having a reaction plane 33 can be controlled in time in the longitudinal direction of the film 34. The capsule medical apparatus 3D further includes an image pickup device and can store captured images.

In this embodiment, one end of the film 34 is wound about an axis of supply 35 disposed near one end (left end in FIG. 6A) of a storage section in a substantial cylindrical form within the exterior 31 and is attached to a driver section 38 such as a cylindrical motor disposed at the position close to the other end, that is the image picking-up side, of the storage section through guide axes (or guide rollers) 37a, 37b and 37c in a storage 36.

Then, rotation of the driver section 38 moves the film 34 wound about the axis of supply 35 to the driver section 38 side so that the film 34 can be sequentially wound about the driver section 38.

The opening part 32 communicates with the outside through a communication path 39 and through an opening 39a at the opposite position of the opening part 32. A suction pump 41 is provided in the middle of the communication path 39.

The suction pump 41 performs a sucking operation under the control of a control circuit 43 to which power is supplied from a battery 42.

By the sucking operation by the suction pump 41, bodily fluids outside are sucked (inhaled) through the opening part 32, and, if an antigen reacting with the reaction plane 33 exposing on the opening part 32 exists, the reaction is promoted. Thus, the bodily fluids sucked to the opening part 32 side are further discharged from the opening 39a at the opposite side of the opening part 32, that is, an exit of the communication path 39. Notably, the control circuit 43 also controls the rotation of the motor of the driver section 38.

In this embodiment, a cleaning bath 44 is provided between the opening part 32 and the driver section 38. The film 34 exposed on the opening part 32 and having undergone an antigen examination is cleaned with a cleaning fluid stored in the cleaning bath 44, and an antigen and an antibody thereon are held at a more stable state so that the detection outside of the body can be performed with high precision.

According to this embodiment, multiple kinds of antibody are fixed to the reaction plane 33 on the film 34 as shown in FIG. 6B so that the multiple kinds of antigen can be detected.

More specifically, the film 34 is divided into four, for example, in the width direction orthogonal to the longitudinal direction (in the vertical direction in FIG. 6B), and an esophagus cancer marker antibody 45a, a stomach cancer marker antibody 45b, a colon cancer marker antibody 45c and a blood component antibody 45d are fixed thereto to form the reaction plane 33. In this case, the esophagus cancer marker may be SCC, CYFRA or the like. The stomach cancer marker may be CEA, CA72-4, CA19-9 or STN. The blood component antibody 45d contains one resulting from the fixing of a chromogen-impregnated tester, for example, in order to detect hemoglobin serving as a oxygen carrier in blood and is analyzed by dropping hydrogen peroxide thereto, measuring an amount of coloring and calculating an amount of hemoglobin.

This embodiment further contains an image pickup device and can store captured images.

For example, in an end on the opposite side of the other end having the axis of supply 35, a hemisphere transparent cover 61 is attached to the opening end of the exterior 31 with, for example, an adhesive in a watertight manner.

A disk-shaped illumination substrate 62 is disposed under the transparent cover 61, and an objective lens frame 63 is fixed in the through-hole at the center of the illumination substrate 62. A first lens 64a and second lens 64b are attached to the objective lens frame 63 to provide an objective optical system (image-forming optical system) 64. The objective lens frame 63 is fixed to the illumination substrate 62 so that the optical axis O of the objective optical system 64 can agree with the longitudinal center axis of the capsule medical apparatus 3D.

Furthermore, Complementary Metal-Oxide Semiconductor (CMOS) imager 65, for example, serving as an image pickup device is disposed at the image-forming position of the objective optical system 64. The CMOS imager 65 is attached to the front surface of an image picking-up substrate 66 disposed on the back surface of the illumination substrate 62. The CMOS imager 65 has an image picking-up plane protected by a cover glass 67.

The image picking-up substrate 66 is integrated with the CMOS imager 65 and the cover glass 67 and has a driving & processing section 68 on the back surface side. The driving & processing section 68 drives the CMOS imager 65 and performs signal processing on image pickup signals output from the CMOS imager 65. An image pickup section 69 includes the CMOS imager 65, cover glass 67, objective optical system 64 and objective lens frame 63.

Illumination sections 71 serving as an illumination unit are attached symmetrically at multiple positions around the optical axis O of the objective optical system 64 on the front surface side of the illumination substrate 62. In FIG. 6A, the letter, O', refers to the center axis (in the direction of outgoing angle 0°) of the emission of illumination light by the light emitting portions of the illumination sections 71, and the letter, φ, refers to an range of light emission of illumination light by the light emitting portions of the illumination sections 71.

A memory 72 is implemented on the back surface, for example, of the image picking-up substrate 66. The memory 72 serves as an image accumulating unit for accumulating (storing) image data resulting from signal processing and compression of image pickup signals of the CMOS imager 65 by the driving & processing section 68.

The image picking-up substrate 66 is connected to the illumination substrate 62 through a flexible substrate 73 for connection. The battery 42 is connected to the image picking-up substrate 66 through a lead wire, not shown, and supplies power for operations to the illumination substrate 62 through the driving & processing section 68 and so on and the flexible substrate 73. The control circuit 43 is electrically connected to the driving & processing section 68 through, for example, a lead wire, not shown, and controls to link operations of the driver section 38 and operations of illumination and image capturing.

Image data accumulated in the memory 72 is retrieved from the capsule medical apparatus 3D excreted from the body of a patient. The image data accumulated in the memory 72 may be read optically through the light-emitting portions of the illumination sections 71, or a contact, for example, for data reading may be provided on the image picking-up substrate 66 to read out the image data.

The CMOS imager 65 serving as an image pickup device is driven through the driving & processing section 68 (under the control of the control circuit 43) to perform image capturing interlocking with the driving of the driver section 38. More specifically, the CMOS imager 65 is driven to pick up the image of an internal part of the lumen when the reaction plane 33 stays still with respect to the opening part 32. Alternatively, the image of an internal part of the lumen may be picked up periodically (more specifically, about 0.1 Hz to 5 Hz).

In the capsule medical apparatus 3D having this construction, the control circuit 43, for example, may intermittently drive by interlocking the driver section 38 and suction pump 41 in time. Alternatively, the driver section 38 may drive at a low speed and intermittently drive the suction pump 41.

In this case, the suction pump 41 is caused to perform a sucking operation so that the residence of bodily fluids on the reaction plane 33 can be prevented, and bodily fluids can be taken into the reaction plane 33 efficiently to promote reaction.

In other words, the suction pump 41 functions to take bodily fluids into the reaction plane 33 and promotes reaction so that the bodily fluids can be discharged quickly through the communication path 39 thereafter and different bodily fluids can be taken into the reaction plane 33.

The control circuit 43 drives the CMOS imager 65 serving as an image pickup device interlocking with an operation of the driver section 38, drives the CMOS imager 65 to pick up the image of an internal part of the lumen when, for example, the reaction plane 33 stays still with respect to the opening part 32 and accumulates image data obtained by the CMOS imager 65 in the memory 72. The capsule medical apparatus 3D is collected after the excretion from the body of a patient, and image data accumulated in the memory 72 is retrieved therefrom.

The film 34 of the reaction plane 33 exposed on the opening part 32 for a predetermined period of time is moved to the driver section 38 side and is cleaned with a cleaning fluid in the cleaning bath 44. Thus, the antigens and antibodies can be held at a more stable state and can be detected outside of the body with high precision.

This embodiment adopts the reaction plane 33 to which multiple kinds of antibodies are fixed so that, when a tumor and/or bleeding exist in different parts in the body, the parts can be identified more easily for detection or analysis.

According to this embodiment, multiple kinds of tumor marker antibody for an esophagus cancer, stomach cancer, colon cancer and so on and multiple kinds of antibody for a blood component and so on are fixed so that, in the detection/ analysis, the part where a cancer occurs can be diagnosed, and the presence of bleeding can be further diagnosed.

Furthermore, since an image at a position having antigen-antibody reaction in the body can be obtained, a diagnosis with higher precision can be performed by combining antigen detection data such as tumor markers, blood components and so on and the image data.

When image capturing is performed interlocking with an operation of the driver section 38 in this embodiment, the image capturing is not performed while the driver section 38 is rotating to wind the film but the image capturing is performed during a time for antigen-antibody reaction where the reaction plane 33 stays still with respect to the opening part 32. Thus, antigen detection data and image data can be compared more easily.

By performing image capturing only during a time when the reaction plane 33 stays still with respect to the opening part 32, images at desired timing can be obtained. Furthermore, the size of the obtained image data can be reduced, which can reduce the capacity of the memory 72.

When image capturing is performed periodically such as at about 0.1 Hz to 5 Hz, images of internal parts of the lumen can be obtained at all times.

Variation Example of Second Embodiment

Instead of accumulating all of image data obtained by an image pickup device in the memory 72 within the capsule medical apparatus 3D, the image data may be temporarily stored in the memory 72, and, when an amount of data is close to the maximum capacity of the memory 72, may be transmitted to the outside of the body by radio through an antenna. Then, the image data may be stored outside of the body.

According to this variation example, the capacity of the memory 72 within the capsule medical apparatus 3D can be reduced. Furthermore, when data transmission can be performed in real time, images of internal parts of the lumen can be monitored outside of the body at all times.

Third Embodiment

Figure 7A:
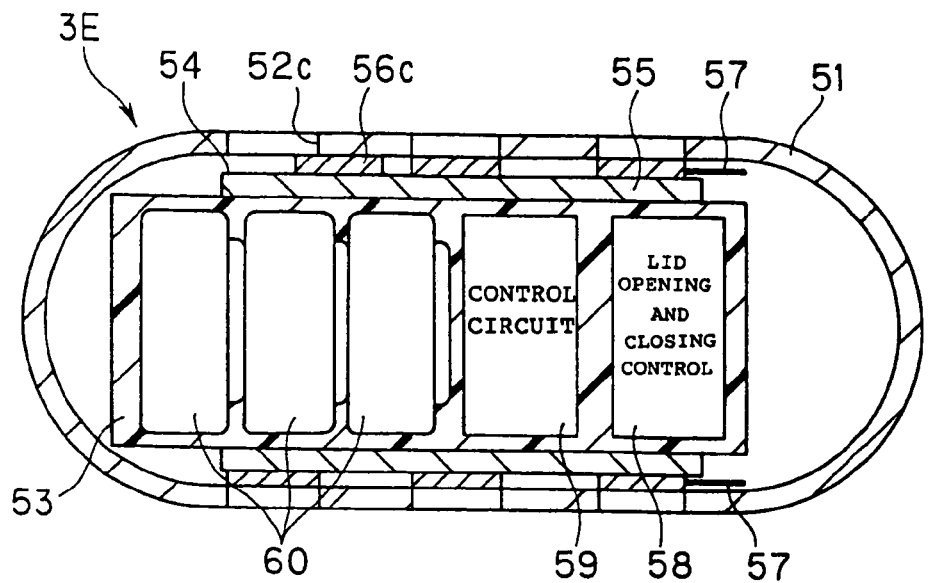
FIG. 7A is a longitudinal section view showing a construction of a capsule medical apparatus according to a third embodiment of the invention.
Figure 7B:
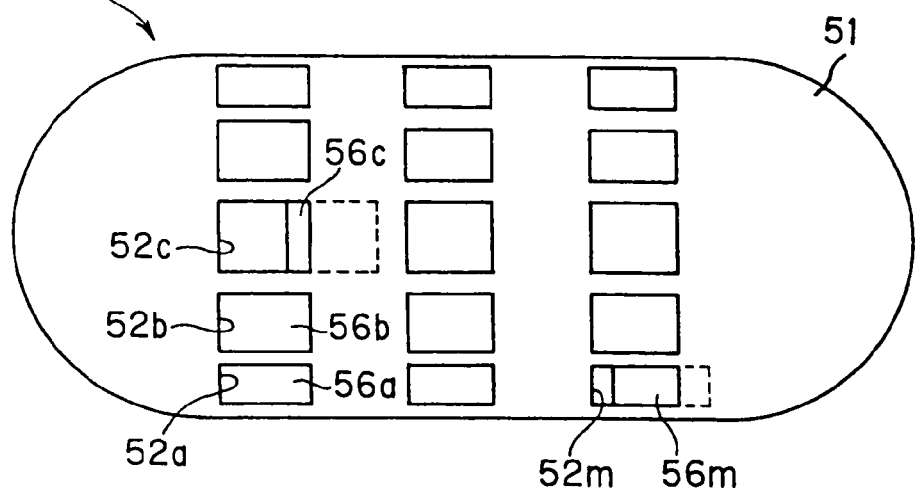
FIG. 7B is a plan view of the capsule medical apparatus in FIG. 7A.
Figure 7C:
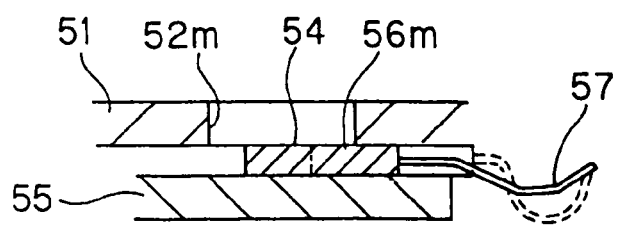
FIG. 7C is an explanatory diagram of an action of the opening and closing of a lid by an ion conducting polymer actuator.

Next, a third embodiment of the invention will be described with reference to FIGS. 7A to 7C. FIG. 7A shows an internal structure of a capsule medical apparatus 3E according to the third embodiment. FIG. 7B shows a plan view of the capsule medical apparatus 3E. FIG. 7C shows an operation of lid opening and closing by an ion conducting polymer actuator.

FIG. 7A shows the capsule medical apparatus 3E according to the third embodiment. The capsule medical apparatus 3E includes, as shown in FIG. 7B, many opening parts 52a, 52b, 52c, . . . on, for example, the cylindrical outer circumference of a capsule-shaped exterior 51.

Under the exterior 51, a film 55 faces toward the opening parts 52a, 52b, 52c, . . . The film 55 has a reaction plane 54 on the cylindrical outer circumference of an internal storage 53.

Many lids 56a, 56b, . . . are disposed between the opening parts 52a, 52b, 52c, . . . and the film 55 and are connected to ion-conducting polymer actuators 57. The lids 56a, 56b, . . . are moved from the opening parts 52a, 52b, 52c, . . . , respectively by the ion-conducting polymer actuators 57 so that the opening and closing of the opening parts 52a, 52b, 52c, . . . can be controlled.

Distal ends of the ion-conducting polymer actuators 57 connecting to the proximal ends of the lids 56a, 56b, . . . are disposed in a space that they can bend, and the space is provided in the distal side in the direction of the movement (right side in FIGS. 7A to 7C). Then, bending the other ends of the ion-conducting polymer actuators 57 move the lids 56i (where $i=a, b, \ldots$) having one ends connected in the direction.

In this case, the driving of the ion-conducting polymer actuators 57 is controlled by a lid opening and closing control circuit 58. The lid opening and closing control circuit 58 is controlled by a control circuit 59 that controls the whole.

The control circuit 59 sends a control signal to the lid opening and closing control circuit 58 such that the opening parts 52a, 52b, 52c, . . . can be opened and closed in time in an order predefined by, for example, a user, and the lid opening and closing control circuit 58 outputs a drive signal (drive voltage) to the ion conducting polymer actuators 57 connecting to the lids 56a, 56b, . . . in accordance with the control signal.

A battery 60 is stored within the internal storage 53. The battery 60 supplies power for operation to the control circuit 59, lid opening and closing control circuit 58 and so on.

FIG. 7C shows an operation of moving the lid 56m covering a part of the opening part 52m shown in FIG. 7B, for example, in response to driving of the ion-conducting polymer actuators 57 by the lid opening and closing control circuit 58.

When the lid opening and closing control circuit 58 outputs drive voltage to the ion conducting polymer actuator 57, the distal side of the ion conducting polymer actuator 57 connecting to the lid 56m bends at a small radius of curvature in a space for bending. Here, the bending part moves to the space side smoothly, and the lid 56m on the proximal side moves at that time. In other words, the lid 56m and ion conducting polymer actuator 57 move from the state indicated by the solid line to the state as indicated by the dashed line.

The unit of moving the lids 56a, 56b, . . . is not limited to the ion conducting polymer actuators 57 but may be a minute linear motor or a polymer piezoelectric element, for example.

According to this embodiment, the many opening parts 52a, 52b, 52c, . . . are provided and the film 55 is provided under the opening parts 52a, 52b, 52c, . . . so as to face toward the reaction plane 54. Furthermore, the lids 56a, 56b, . . . are movable between the opening parts 52a, 52b, 52c, . . . and the reaction plane 54 so that the respective opening parts 52a, 52b, 52c, . . . can be opened and closed.

Thus, multiple kinds of antibody are fixed onto the reaction plane 54 facing toward the opening parts 52a, 52b, 52c, . . . like the second embodiment so that the multiple kinds of antigen can be detected like the second embodiment.

Furthermore, according to this embodiment, the opening and closing of the opening parts 52a, 52b, 52c, . . . can be controlled in more detail in accordance with a part to be examined and/or a speed of movement of the capsule medical apparatus 3E.

While the esophagus cancer marker may be SCC, CYFRA or the like and the stomach cancer marker may be CEA, CA72-4, CA19-9 or STN, they are not limited to these tumor markers. CEA, AFP, CA125, CA72-4, CA19-9, STN, SCC antigen, NCC-ST-439, CYFRA, DuPan-2 or the like may be used instead.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule medical device comprising:
a capsule enclosure with an exterior surface;

a reaction plane on an interior surface within the exterior surface, the reaction plane having one or more types of reactive substances that bind in a specific manner to an internal bodily substance, the capsule enclosure containing an opening in the exterior surface for bodily fluid to contact the reaction plane;

an exposure controller for controlling exposure of the reaction plane to the bodily substances; and an internal driver for moving the interior surface holding the reaction plane relative to the exterior surface.

2. The capsule medical device according to claim 1, wherein the reacting substance fixed on the reaction plane is an antibody that specifically reacts with an antigen such as a tumor marker and a blood component.

3. The capsule medical device according to claim 1, wherein the reacting substance fixed on the reaction plane is protein that reacts with an internal substance such as a tumor marker and a blood component.

4. The capsule medical device according to claim 1, wherein the reaction plane is provided on the outer surface of the capsule medical device.

5. The capsule medical device according to claim 1, wherein the reacting substance on the reaction plane is a magnetic antibody which is fixed to the reaction plane by a magnetic substance.

6. The capsule medical device according to claim 1, wherein the capsule medical device has a reclosable lid serving as the exposure controller.

7. The capsule medical device according to claim 1, wherein a time indicator is provided on the reaction plane.

8. The capsule medical device according to claim 1, wherein the capsule medical device includes an image pickup device, an image-forming optical system that forms an image of a subject in the image pickup device and an image accumulating section that accumulates data of biological information obtained by the image pickup device.

9. The capsule medical device according to claim 1, wherein a filter for filtering bodily fluids is provided between the reaction plane and the outer surface of the capsule medical device.

10. The capsule medical device according to claim 1, wherein the capsule medical device includes a cleaning section for cleaning the reaction plane having reacted with bodily fluids.

11. The capsule medical device according to claim 1, wherein the capsule medical device has at least one of a sucking section that sucks bodily fluids and a discharging section that discharges bodily fluids.

12. The capsule medical device according to claim 1, further comprising a preserving section in which a part of the reaction plane that is not exposed in the exposure controller is filled with a preservative fluid.

13. The lesion detecting system according to claim 1, wherein the reaction part is removably provided to the capsule medical apparatus.

14. The capsule medical device according to claim 4, wherein the capsule medical device includes an image pickup device, an image-forming optical system that forms an image of a subject in the image pickup device, and an image accumulating section that accumulates data of biological information obtained by the image pickup device.

15. The capsule medical device according to claim 14, wherein the image pickup device periodically captures images.

16. The capsule medical device according to claim 14, wherein the capsule medical device has a transmitter that transmits data of biological information.

17. The capsule medical device according to claim 5, wherein the magnetic substance is a permanent magnet.

18. The capsule medical device according to claim 5, wherein the magnetic substance is a magnetic film.

19. The capsule medical device according to claim 6, wherein multiple reclosable lids each serving as the exposure controller are provided on the outer surface of the capsule medical device.

20. The capsule medical device according to claim 8, wherein the image pickup device and the exposure controller are cooperatively controlled by a control circuit when capturing images.

21. The capsule medical device according to claim 8, wherein the capsule medical apparatus-device has a transmitter that transmits data of biological information.

22. The capsule medical device according to claim 20, wherein the image pickup device captures images periodically.

23. The capsule medical device according to claim 9, wherein the filter is made of a material that biological substances do not adhere to and coagulate in.

24. A lesion detecting method, comprising the steps of:
providing a capsule medical device, the capsule medical device comprising:
a capsule enclosure with an exterior surface;
a reaction plane on an interior surface within the exterior surface, the reaction plane having one or more types of reactive substances that bind in a specific manner to an internal bodily substance, the capsule enclosure containing an opening in the exterior surface for bodily fluid to contact the reaction plane;
an exposure controller for controlling exposure of the reaction plane to the bodily substances; and
an internal driver for moving the interior surface holding the reaction plane relative to the exterior surface;
swallowing the capsule medical device;
causing the reaction plane to react in a living body;
collecting the capsule medical device that is excreted from the body; and
analyzing the reaction plane of the collected capsule medical device.

25. The lesion detecting method according to claim 24, wherein the step of causing the reaction part to react in the body to be examined is:
a step of causing reaction between a fixing section that a chemical reacting substance or biochemical reacting substance is fixed provided on the reaction part and an internal substance.

26. The lesion detecting method according to claim 24, wherein the step of causing the reaction part to react in the body to be examined includes one or more cycles of the steps of:
exposing the fixing section that a chemical reacting substance or biochemical reacting substance is fixed provided on the reaction part so as to react with an internal substance; and
causing reaction between an exposed part and an internal substance.

27. The lesion detecting method according to claim 24, wherein the step of causing the reaction part to react in the body to be examined includes one or more cycles of the steps of:
exposing the fixing section that a chemical reacting substance or biochemical reacting substance is fixed provided on the reaction part so as to react with an internal substance;

causing reaction between an exposed part and an internal substance; and cleaning the fixing section after reaction.

28. The lesion detecting method according to claim 24, wherein the step of causing the reaction part to react in the body to be examined includes one or more cycles of the steps of:

exposing the fixing section that a chemical reacting substance or biochemical reacting substance is fixed provided on the reaction part so as to react with an internal substance;

causing reaction between an exposed part and an internal substance; and causing reaction between the fixing section after reaction and a preservative substance.

29. The lesion detecting method according to claim 24, wherein the step of causing the reaction part to react in the body to be examined includes one or more cycles of the steps of:

exposing the fixing section that a chemical reacting substance or biochemical reacting substance is fixed provided on the reaction part so as to react with an internal substance;

sucking an internal substance to the fixing section; and causing reaction between an exposed part and an internal substance.

30. The lesion detecting method according to claim 24, wherein the step of analyzing includes the steps of:

bonding labeled molecules to reacting molecules on the reaction part;

cleaning unbonded labeled molecules;

measuring an amount of bonded labeled molecules; and performing a diagnosis based on a measurement result thereof.

31. The lesion detecting method according to claim 24, wherein the analyzing step comprises a step of cleaning the reaction part.

32. The lesion detecting method according to claim 26, wherein the analyzing step comprises a step of detecting a position where the reaction part reacted in the body.

33. The lesion detecting method according to claim 32, wherein the analyzing step further comprises a step of calculating a time when the detected position reacted in the body.

34. A lesion detecting system comprising:

a capsule medical device comprising a capsule enclosure with an exterior surface, a reaction plane on an interior surface within the exterior surface, the reaction plane having one or more types of reactive substances that bind in a specific manner to an internal bodily substance, the capsule enclosure containing an opening in the exterior surface for bodily, fluid to contact the reaction plane, an exposure controller for controlling exposure of the reaction plane to the bodily substances, and an internal driver for moving the interior surface holding the reaction plane relative to the exterior surface; and an analyzer for detecting and analyzing the substance reacted with the reaction plane or a trace of the reaction outside of the body to be examined.

* * * * *